US008293814B2

(12) United States Patent
Cardinali

(10) Patent No.: US 8,293,814 B2
(45) Date of Patent: Oct. 23, 2012

(54) BIODEGRADABLE PRODUCT OBTAINED FROM COMPOUNDS OF THERMOPLASTIC POLYMERS

(75) Inventor: Bruno Cardinali, Fermo (IT)

(73) Assignee: Tecnofilm S.p.A., Sant Elpidio a Marem (IT)

( * ) Notice: Subject to any disclaimer, the term of this patent is extended or adjusted under 35 U.S.C. 154(b) by 0 days.

(21) Appl. No.: 12/932,590

(22) Filed: Mar. 1, 2011

(65) Prior Publication Data
US 2011/0160335 A1 Jun. 30, 2011

(30) Foreign Application Priority Data

Nov. 12, 2009 (IT) .............................. MC2009A0230
Oct. 26, 2010 (EP) ..................... 10188829

(51) Int. Cl.
C08K 5/00 (2006.01)
C08K 5/05 (2006.01)
C08K 5/06 (2006.01)
(52) U.S. Cl. ............................. 523/124; 524/1; 524/114
(58) Field of Classification Search .................. 523/124; 524/1, 114
See application file for complete search history.

(56) References Cited

U.S. PATENT DOCUMENTS

| 5,703,160 A | 12/1997 | Dehennau et al. |
| 2009/0123728 A1* | 5/2009 | Cheung et al. ............. 428/304.4 |
| 2009/0234035 A1* | 9/2009 | Cheung et al. .................. 521/81 |

FOREIGN PATENT DOCUMENTS

| EP | 0 470 691 A2 | 2/1992 |
| EP | 0470691 A2 | 2/1992 |
| EP | 1441031 A1 | 7/2004 |
| JP | 6-322216 A | 11/1994 |
| JP | 0632216 | 11/1994 |
| WO | 2007-125546 A1 | 11/2007 |
| WO | WO 2007/012546 A1 | 11/2007 |
| WO | 2008-087675 A1 | 7/2008 |

OTHER PUBLICATIONS

European Search Report for EP 11 15 9529 dated Jun. 29, 2011.
European Search Report for EP 10 18 8829 dated Dec. 30, 2010.

* cited by examiner

Primary Examiner — Kriellion Sanders
(74) Attorney, Agent, or Firm — Lowe Hauptman Berner & Ham LLP

(57) ABSTRACT

A biodegradable product obtained from compounds of thermoplastic polymers is described, comprising: a styrenic block copolymer, a plasticizer, and a biodegradation catalyst, in which the plasticizer is a natural oil and the biodegradation catalyst is a yeast.

20 Claims, No Drawings

BIODEGRADABLE PRODUCT OBTAINED FROM COMPOUNDS OF THERMOPLASTIC POLYMERS

The present patent application for industrial invention relates to the sector of compounds of thermoplastic polymers and in particular to compounds of styrenic block copolymers that can be used to obtain biodegradable products without the need to adopt special procedures for biodegradation of said products.

SBS (Styrene-Butadiene-Styrene), SIS (Styrene-Isoprene-Styrene), SIBS (Styrene-Isoprene, Butadiene-Styrene) styrenic block copolymers and relevant hydrogenated derivatives (SEBS, SEPS, etc.) are usually plasticized with mineral oils of paraffinic type with low content of aromatic products.

Said block copolymers are suitably formulated with various additives, extenders, reinforcing agents, pigments, etc. of organic or inorganic type and are subject to a compounding process to form compounds that are used in many industrial sectors, such as shoes, car components, toys, seals, etc. in order to obtain technical products with average life longer than one year.

Being thermoplastic elastomeric materials, said compounds have considerable applicative advantages compared to vulcanized elastomers; therefore their use is constantly growing, reducing the market share of reticulated rubbers.

One of the problems, which is also common to vulcanized elastomeric products, is poor biodegradability, since the presence of mineral oils in the products enormously reduces their environmental degradability capacity.

The use of plasticizers, fillers or extenders, with structures with organic base, such as oils extracted from a large variety of vegetal organisms—soya bean, corn, flax, etc. as well as starch and cellulose—contributes to solve at least partially the problems created by mineral plasticizers, that is to say the problem of human contact and biodegradability.

The international patent applications WO2008/087675 and WO2009/152870, in the name of the same applicant, perfectly describe the state of the art with regard to the aforementioned problems. In any case, the compounds describes in these two patent applications are not biodegradable according to ISO 14855, since the base polymer part, which qualifies the family of these products and gives them their essential chemical-physical characteristic, is not subject to biodegradation such to achieve the 90% required by the standards in a determined period of time.

EP 0 726 325 describes a decomposition process of a polycarbonate resin that is a special Polyester. This process provides for adding enzymes at the end of the product life cycle, that is to say when the product must be disposed of. Therefore, this document does not describe a product that is biodegradable by itself and the enzymes are not mixed to the compound to obtain the product. On the other hand, a polyester product is more biodegradable than a product obtained with compounds of styrenic block copolymers. Therefore the problem to obtain a more biodegradable problem does not exist.

JP 6 322216 describes a method to make a polyvinyl alcohol (PVA) biodegradable, which provides for coating the surface of the final product with micro-organisms. Also in this case, the micro-organisms are not mixed to the compound and the polyvinyl alcohol is different from thermoplastic polyoleofins.

In fact, the same document asserts that the results obtained to make polyoleofins biodegradable with micro-organisms are not satisfactory.

JP 2002 362578 describes the production of plastic bags made of polyethylene succinate (polyester), in which a large quantity of yeast is added to make them strongly biodegradable. It must be considered that the ester group is easily decomposable with respect to styrenic block copolymers. Moreover, a biodegradable plastic bag has a very short average life, since it is generally disposable or used for a few times before disposal. Therefore such polyester is not suitable for technical products having a much longer life.

JP 2007 063297 describes a synthesis process of an easily decomposable and biodegradable polyester. The degradation of the product at the end of the life cycle can be carried out with micro-organisms.

The purpose of the present invention is to solve the drawbacks of the prior art by devising a biodegradable product obtained from compounds of thermoplastic polymers that is suitable to be used in technical sectors with average life longer than five years and at the same time such a product that can be biodegraded rapidly at the end of its life cycle.

Said purpose has been achieved according to the invention with the characteristics described in the enclosed independent claim 1.

Advantageous embodiments of the invention are disclosed in the dependent claims.

According to the invention, the biodegradable product obtained from compounds of thermoplastic polymers comprises at least one styrenic block copolymer, a plasticizer and a catalyst for biodegradation.

The plasticizer is natural oil and the biodegradation catalyst is a yeast.

The styrenic block copolymer is in weight percentage between 20 and 70%, preferably 50-60% with respect to the total weight of the biodegradable product.

Natural oil is in weight percentage between 10% and 60%, preferably 40-50% with respect to the total weight of the biodegradable product.

Yeast is in weight percentage of 0.5-4% with respect to the total weight of the biodegradable product.

The biodegradable product of the invention can be a biodegradable compound that is used for production of a finished product or it can be a biodegradable finished product obtained from a non-biodegradable compound to which yeast is added. The finished product has an average life longer than five years.

Amongst styrenic block copolymers, SBS (Styrene-Butadiene-Styrene) is preferably used.

However, also products correlated to SBS and their combinations can be used, such as SIS (Styrene-Isoprene-Styrene) or SBS (Styrene-Butadiene, Isoprene-Styrene). Moreover, hydrogenated homologues of SBS can be used, which are SBS block copolymers, the aliphatic unsaturated chain of which is hydrogenated, such as SEBS (Styrene-Ethylene, Butylene-Styrene), SEPS (Styrene-Ethylene, Propylene-Styrene), SEEPS (Styrene-Ethylene, Ethylene, Propylene-Styrene).

Amongst natural oils, mixed colza and soya bean oil is preferably used. However, only colza oil or only soya bean oil can be used. Other vegetal oils of any origin can be used, such as palm oil, peanut oil, corn oil and similar oils.

Amongst yeasts, brewer's yeast is preferably used, being the easiest product to find on the market. However, other yeasts can also be used, in solid or liquid form, such as natural yeast or yeast mother.

Advantageously, modified yeasts can be used to reduce the typical odor of yeast, such as partially hydrolyzed yeasts.

For realization of a biodegradable compound, the styrenic block copolymer, natural oil and brewer's yeast are mixed to obtain a semifluid product that is extruded at a temperature of about 120-180° C., in such a way to obtain granules or pallets that form the biodegradable compound containing the yeast. The biodegradable compound can be used in an extrusion or molding process to obtain a final biodegradable product containing yeast.

Alternatively, the compound can be realized using only the styrenic block copolymer and natural oil. In such a case, when the final biodegradable product is to be realized, yeast is added to the compound during the extrusion or molding process to realize the final biodegradable product. In such a case, the yeast that is added always has a weight percentage of about 0.5-4%, with respect to the final biodegradable product and in any case the yeast is perfectly amalgamated with the final product.

The yeast carries out a catalytic action on organic products (natural oil) and allows the material obtained with such a compound to exceed the biodegradation threshold of 90% of total, in a variable number of months according to the polymer structure and vegetal contents of the compound. The above means that there is a synergic action between yeast and natural oil. The final product is biodegradable in the conditions established by ISO 14 855.

Following are some examples of biodegradable compounds according to the invention.

| EXAMPLE 1 (COMPOUND-EP1) | Kg |
|---|---|
| SBS, such as SOL T 161 | 100 |
| Mixed COLZA and SOYA BEAN oil | 80 |
| Brewer's yeast | 2.0 |

These components were mixed and extruded to obtain a biodegradable compound (EP1). The biodegradable compound (EP1) was molded to obtain samples that underwent various tests and showed the following features:

Features

| Features | |
|---|---|
| Shore A | 30 |
| MI (190°/5/Kg) | 25 |
| Tensile Strength at Break (Mpa) | 4.5 |
| Elongation (%) | 800 |
| Biodegradation according to ISO 14855 at 90% | months 4 |

| EXAMPLE 2 (COMPOUND-EP2) | Kg |
|---|---|
| SBS, type SOL T 161 | 100 |
| Mixed COLZA and SOYA BEAN oil | 80 |
| PS Crystal | 30 |
| Brewer's yeast | 2.0 |

The biodegradable compound (EP2) differs from the first compound (EP1) for the presence of Polystyrene (PS) Crystal that is used to increase the hardness of the final product, as shown by the features indicated below:

Features

| Features | |
|---|---|
| Shore A | 60 |
| MI | 50 |
| Tensile Strength at Break | 4.5 |
| Elongation (%) | 500 |
| Abrasion (mm$^3$) | 20 |
| Biodegradation according to ISO 14855 at 90% | months 6 |

The addition of PS crystal in the compound (EP2) resulted in prolongation of biodegradation by two months with respect to compound (EP1).

To obtain a higher hardness of the final product, the Polystyrene (PS) Crystal must be comprised between 2 and 30%, preferably 10-20% of the compound.

To obtain the same result, instead of polystyrene crystal or polystyrene anti-shock, other polymers can be used, such as: Syndiotactic Polybutadiene 1-2 in quantity between 5-30% or Poly-ethylene-vinylacetate (EVA) or Poly ethylene-methylacrylate (EMA) or Poly ethylene-Butyl acrylate (EBA) in quantity comprised between 2-5%.

EXAMPLE 3

Same as EXAMPLE 2, with brewer's yeast replaced with natural yeast. Biodegradation according to ISO 14855 at 90% of 4 months was obtained. In this specific case, natural yeast gave a better biodegradability result than brewer's yeast.

EXAMPLE 4

Same as EXAMPLE 2, with brewer's yeast replaced with amylase enzyme. Biodegradation according to ISO 14855 at 90% of 12 months was obtained.

As shown by example 4, the use of an enzyme gave a less satisfactory result than the yeast.

The invention claimed is:
1. A biodegradable product obtained from a plasticized polymer comprising:
a styrenic block copolymer,
a plasticizer, and
a biodegradation catalyst,
wherein
the plasticizer is a natural oil, and
the biodegradation catalyst is a yeast.
2. The biodegradable product as claimed in claim 1, wherein concentration in weight percentage of said yeast ranges between 0.5 and 4% with respect to the total weight of the biodegradable product.
3. The biodegradable product as claimed in claim 1, wherein said yeast comprises brewer's yeast and/or natural yeast.
4. The biodegradable product as claimed in claim 1, wherein said yeast comprises a partially hydrolyzed yeast.
5. The biodegradable product as claimed in claim 1, wherein concentration in weight percentage of said natural oil ranges between 40 and 50% with respect to the total weight of the biodegradable product.
6. The biodegradable product as claimed in claim 1, wherein said natural oil comprises colza oil and/or soya bean oil.
7. The biodegradable product as claimed in claim 1, wherein concentration in weight percentage of said styrenic block copolymer ranges between 50 and 60% with respect to the total weight of the biodegradable product.

8. The biodegradable product as claimed in claim 1, wherein said styrenic block copolymer is Styrene-Butadiene-Styrene (SBS).

9. The biodegradable product as claimed in claim 1, wherein the biodegradable product further comprises a polymer other than the styrenic block copolymer in an amount sufficient to increase hardness of the biodegradable product.

10. The biodegradable product as claimed in claim 1, wherein the biodegradable product is obtained from mixing a styrenic block copolymer, a natural oil and a yeast to obtain a semisolid product that is extruded to obtain granules or pellets of said biodegradable product.

11. The biodegradable product as claimed in claim 1, wherein the biodegradable product is a finished product.

12. The biodegradable product as claimed in claim 1, wherein the biodegradable product is a obtained by extrusion or molding of a composition comprising a styrenic block copolymer and natural oil, to which yeast is added during extrusion or molding.

13. The biodegradable product as claimed in claim 9, wherein the polymer is Polystyrene (PS) Crystal, Syndiotactic Polybutadiene 1-2, Poly-ethylene-vinylacetate (EVA), Poly ethylenemethylacrylate (EMA), or Poly ethylene-Butyl acrylate (EBA).

14. The biodegradable product as claimed in claim 13, wherein the polymer is Polystyrene (PS) Crystal.

15. The biodegradable product as claimed in claim 14, wherein the polystyrene crystal (PS) is present in a weight concentration ranging from 10 to 20% with respect to the biodegradable product.

16. The biodegradable product as claimed in claim 1, wherein the biodegradable product is biodegradable according to the conditions established by ISO 14855.

17. The biodegradable product as claimed in claim 11, wherein the biodegradable product is biodegradable according to the conditions established by ISO 14855.

18. The biodegradable product as claimed in claim 12, wherein the biodegradable product is biodegradable according to the conditions established by ISO 14855.

19. A biodegradable product obtained from a plasticized polymer comprising:
    a styrenic block copolymer present in a weight concentration ranging from 20 to 70% with respect to the total weight of the biodegradeable product;
    a plasticizer chosen from natural oils present in a weight concentration ranging from 10 to 60% with respect to the total weight of the biodegradeable product; and
    a biodegradation catalyst chosen from yeasts present in a weight concentration ranging from 0.5 to 4% with respect to the total weight of the biodegradeable product;
    wherein the biodegradable product is in the form of a finished product having an average life longer than five years; and
    wherein the biodegradable product is biodegradable according to the conditions established by ISO 14855.

20. A biodegradable product obtained from a plasticized polymer comprising:
    a styrenic block copolymer present in a weight concentration ranging from 50 to 60% with respect to the total weight of the biodegradeable product;
    a plasticizer chosen from natural oils present in a weight concentration ranging from 40 to 50% with respect to the total weight of the biodegradeable product;
    a biodegradation catalyst chosen from yeasts present in a weight concentration ranging from 0.5 to 4% with respect to the total weight of the biodegradeable product; and
    polystyrene (PS) crystal in a weight concentration ranging from 2 to 30% with respect to the total weight of the biodegradeable product;
    wherein the biodegradable product is in the form of a finished product having an average life longer than five years; and
    wherein the biodegradable product is biodegradable according to the conditions established by ISO 14855.

\* \* \* \* \*